United States Patent [19]

Plusquellec et al.

[11] Patent Number: 5,223,411
[45] Date of Patent: Jun. 29, 1993

[54] NONIONIC SURFACTANTS HAVING A CARBAMOYL GROUP AND PROCESS FOR TREATMENT OF A PROTEINS CONTAINING MEDIUM USING THE SAME

[75] Inventors: Daniel Plusquellec, Noyal sur Seiche; Henri Wroblewski, Rennes, both of France

[73] Assignee: Centre National de la Recherche Scientifique (CNRS), Paris, France

[21] Appl. No.: 523,127

[22] Filed: May 14, 1990

[51] Int. Cl.⁵ .................... C12P 21/04; C12R 1/01
[52] U.S. Cl. ........................ 435/71.2; 435/71.1; 435/71.3; 435/822; 536/4.1
[58] Field of Search .............. 435/71.2, 71.1, 71.3, 435/822; 536/4.1

[56] References Cited

U.S. PATENT DOCUMENTS 4,315,919  2/1982  Shanbrom ............... 435/71.1
4,582,799  4/1986  Jarvis ..................... 435/71.3
4,959,459  9/1990  David et al. ............ 536/41.

OTHER PUBLICATIONS

CA Computer Abstract (CA91) CA111 (7):53659p Plusquellec et al. "Anal. Biochem." 179(1), 145-5-3-[1989].
CA Computer Abstract (CA91) CA113 (17):152900h Plusquellec et al. "Tetrahedron" 46(2) 465-74 [1990].
CA Computer Abs. CA 109(9):73772g Plusquellec et al. "Tetraheron Lett." 28(36) 4165-8 [1987].
"Guide to Properties & Uses of Detergents in Biology & Biochemistry" Neugebauer 1987 [Hoechst Celanese Corp] pp. 19, 27, 45-55.

*Primary Examiner*—Herbert J. Lilling
*Attorney, Agent, or Firm*—Dressler, Goldsmith, Shore, Sutker & Milnamow, Ltd.

[57] ABSTRACT

The present invention relates to non ionic surfactants having the general formula (I):

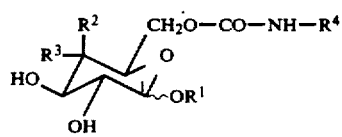

wherein:
$R^1$ is H or CH3
$R^2$ is H or OH
$R^3$ is H or OH
$R^4$ is an alkyl of formula $-(CH_2)_n-CH_3$ wherein n is an integer comprised between 6 and 20

It also relates to a process for treatment of proteins containing medium without denaturation of said proteins, using these surfactants.

3 Claims, No Drawings

NONIONIC SURFACTANTS HAVING A CARBAMOYL GROUP AND PROCESS FOR TREATMENT OF A PROTEINS CONTAINING MEDIUM USING THE SAME

SUMMARY OF THE INVENTION

This invention relates to a new family of non ionic surfactants. These surfactants can be used for extracting membrane proteins from lipid membranes.

The invention relates too to a process for treating a medium which contains proteins, without denaturing the proteins.

In particular, this invention relates to a process for extracting membrane proteins from microorganisms.

Surfactants can find a wide range of applications and it was one of the purposes of these last few years to synthesize new molecules, with more appropriate characteristics for their desired use.

Notably, a useful application is the extraction of membrane proteins. The purification of membrane proteins is an essential step in determining their structure and elucidating their function. Since integral membrane proteins are more or less embedded within the lipid bilayer, extraction under a soluble form is a prerequisite for their purification.

Solubilization of these proteins is best achieved with surfactant.

As far as proteins concerned are proteins from the membrane of microorganisms, they could be extracted from a complex medium.

A good surfactant should allow proteins to be obtained under a fully dissociated state without undesirable side effects, such as the loss of activity due or not due to denaturation. Furthermore, proteins of the medium will not either be altered.

Another application of these surfactants can be, after extraction of the membrane proteins, from viruses, to form particles having the same membrane structure as the infectious virus, but devoid of pathogenicity.

Thus, the surfactant should be easy to remove from the preparations and not interfere with protein detection by UV light absorption or with protein titration. Also, it should not modify the charge properties of proteins, be highly soluble in water and different types of buffers and be available, if possible, at low cost.

The new surfactants synthesized during recent years include alkyl glucosides, alkyl thioglucosides, zwitterionic surfactants, surfactants containing a gluconamide polar group and alkanoyl-N-methylglucamides. Although these compounds, notably the last ones, possess most of the desirable properties, an all-purpose surfactant is not available. Indeed, faults and qualities are permutable according to the experimental context. For example, the low temperature cloud point of Triton X-114 proved useful for the separation of amphiphilic proteins from water-soluble ones. In the same way, the strongly denaturing properties of sodium dodecyl sulfate (SDS) are exploited in SDS-polyacrylamide gel electrophoresis, a very widely used technique for the separation of proteins. Furthermore, the ability to extract membrane proteins with selectivity, an operation very useful for their purification, depends on both the intrinsic properties of the surfactant and the membrane itself.

Thus, to cope efficiently with the diversity and complexity of the problems encountered, it is necessary to design and synthetize new surfactants.

DETAILED DESCRIPTION OF THE INVENTION

The present invention relates to non ionic surfactants having the general formula (I):

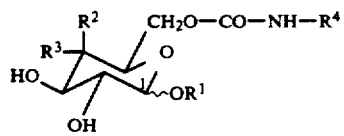

wherein
$R^1$ is H or CH3
$R^2$ is H or OH
$R^3$ is H or OH
$R^4$ is an alkyl of formula $(CH_2)_n CH_3$ wherein n is an integer comprised between 6 and 20

The hydrophilic moiety is represented by an aldohexose, e.g. D-glucose, D-galactose or methyl α-D-glucoside.

The molecule possesses a carbamoyl group between the hydrophobic and hydrophilic moiety. The hydropholic moiety is an alkyl chain.

Preferably, n is comprised between 6 to 10.

The reaction to obtain these compounds is relatively easy and inexpensive to perform. The primary hydroxyl groups of aldohexoses add selectively to alkylisocyanates, the temporary protection of the other hydroxyls of the starting sugars being not necessary.

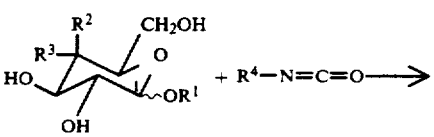

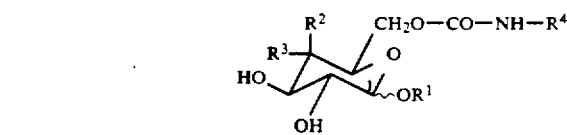

The reaction is performed in anhydrous pyridine, at room temperature, within 15/20 hours. The solvent is then evaporated, and the residue diluted with water and n-butanol. After washing and evaporation of the solvent, the residue is subjected to silica gel column, chromatography or crystallization.

This synthesis method give high yields of the carbamate derivative, because there is a lack of by products in this addition and carbamate is easily purified by silica gel column, chromatography and recrystallization. It can be used for the carbamoylation of the primary hydroxyl of various mono and oligosaccharides.

In particular, it can lead to non ionic surfactant for which in the formula I, $R^2$ is H, $R^3$ is OH and $OR^1$ is in α position on the carbon 1.

Preferably, the invention relates to a non ionic surfactant of the formula I wherein $OR^1$ is in α position, $R^1$ is CH3, $R^2$ is H, $R^3$ is OH and n=6; this surfactant is 6-0-(N-Heptylcarbomoyl) methyl-α-D-glucopyranoside, so-called HECAMEG.

HECAMEG, molar mass 335.38, can be synthesized by a simple and low cost procedure from methyl-α-D-glucopyranoside.

This surfactant is characterized by a high solubility in water (even at 0° C.). Its solubility is higher than 60 g/l in currant buffers, at 4° C. It is stable several weeks at 4° C.

It is transparent for ultravioletlight in the regions useful for protein detection. It is colorimetrically titrable by the anthrone technique and is weak interference in protein titration by the Lowry et al. procedure and the bicinchronimic method is easy to overcome.

Its critical micellar concentration (CMC) is 19.5 mM (6.5 g/l), thus allowing its fast elimination by dialysis or ultrafiltration, unlike the others non ionic surfactants. This CMC is intermediate between that of zwitterionic surfactants (8-9 mM) and OG (25 mM).

Furthermore it is a well defined non ionic detergent permitting to reproduce rigourously experiments. It does not denature proteins, and does not interfere with their biological properties and enzymatic activities. It achieves dissociation of agregated proteins.

This invention relates to process for treatment of a proteins containing medium without denaturation of said proteins, useful in particular for extracting surface membrane proteins from microorganisms present in a complex medium, comprising contracting micro- organisms with an effective amount of at least one surfactant of general formula 1, for sufficient period of time.

Preferably, it relates to a process as defined above, wherein surfactant is 6-0-(N-Heptylcarbamoyl) methyl α-D-glucopyranoside.

In a particular embodiment of this process microorganisms are bacteria. These bacterial can be selected from the group consisting of *Halobacterium halobium*, *Spiroplasma melliferum* and *Pasteurella multocida*.

These surfactants, particularly HECAMEG, are very mild toward protein structure and function.

The usefulness of HECAMEG for membranes studies was ascertained by analyzing its effect on the membranes of *H. halobium* and *S. milliferum*. The surfactant showed a good solubilizing power since it was able to extract 75% of bacteriorhodopsin from the purple membrane of *H. halobium* and 40% of protein from the spiroplasmal membrane.

In the latter case, the major protein, spiralin, was quantitatively extracted with a high degree of selectivity, approaching that obtained with zwitterionic detergents. This property is very promising in the perspective of using this surfactant for the purification of membrane proteins. Furthermore, spectral and antigenic properties of, respectively, bacteriorhodopsin and spiralin indicated that these two membrane proteins were solubilized under a form similar or very close to the native state. Indeed, the spectrum of bacteriorhodopsin extracted with HECAMEG was similar to that observed with nondenaturing surfactants and quite different from that obtained with denaturing surfactants such as SDS.

In the case of spiralin, since the immunoprecipitate obtained by crossed immunoelectrophoresis in the presence of HECAMEG was sharp and heavy, it is improbable that the protein has undergone important structural modifications upon solubilization.

The mildness of HECAMEG toward proteins was confirmed by analyzing its effects on four enzyme activities. The two membrane enzymes NADH oxidase and succinate dehydrogenase were not inhibited by the surfactant. On the contrary, an apparent activation was observed, probably due to an optimization of the interaction between the enzymes and their substrates after the solubilization of the former.

This interpretation is in agreement with the fact that this "activation" phenomenon was observed only when the surfactant was used above its CMC, which actually corresponds to the conditions required for membrane solubilization.

In the case of the two soluble enzymes lactoperoxidase and -lactamase, opposite effects were recorded above the CMC, since -lactamase activity decreased while that of lactoperoxidase increased. In fact, the apparent inhibition of the former did not necessarily reflect a direct effect of the surfactant on the enzyme but, probably, an interaction between surfactant micelles and reactives.

This interpretation is substantiated by the fact that above the CMC, HECAMEG modified the spectral properties of both the substrate (Nitrocefin) and the product of the reaction, suggesting that the reactives were sequestered by surfactant micelles.

The following examples illustrate the invention without limiting the scope thereof.

EXAMPLE 1

Synthesis of 6-0 (N-Heptylcarbamoyl) methyl α-D-glucopyranoside (HECAMEG)

Heptylisocyanate 2 was synthesized from octanoyl chloride according to Allen and Bell and freshly distilled before use (bp, 81° C., 19 mm Hg; yield 71%). HECAMEG was synthesized from methyl-α-D-glucoside and heptylisocyanate. Thus, 20 mmol of methyl--D-glucoside was dissolved in 20 ml or anhydrous pyridine. The solution was then cooled at 0°-5° C. and 10 mmol of heptylisocyanate was added dropwise under vigorous stirring and with exclusion of moisture. The reaction was performed overnight at room temperature. Two main spots corresponding to the expected carbamate (Rf=0,47) and residual methyl-α-D-glucoside (Rf=O,13) were detected by thin-layer chromatography. The solvent was removed by evaporation at 35°-40° C. under vacum, and the remainder was diluted with 50 ml of 50 mM. Kphosphate buffer (pH 7.0) and extracted three time with 30 ml of ethyl acetate. The extract was washed twice with water and dried over anhydrous MgSO$_4$, and the solvent was evaporated.

The residue was subjected to chromatography on a silica gel column (100 g) equilibrated with ethyl acetate to separate the carbamate from a small amount of diheptylurea. The mixture was eluted with 100 ml of ethyl acetate, then 200 ml of a mixture of ethyl acetate and methanol (98/2, v/v), and finally 400 ml of ethyl acetate and methanol (9/1, v/v). The solvent was evaporated and the oily carbamate (3.08 g; yield, 92%) was recrystallized twice from ethyl acetate, mp 108°-110° C., (a) DD$^{22}$ =89±2 (C=9,42×10−3, H$_2$0). The carbamate (yield 52% ) formed white needles which proved chemically homogeneous in $^1$H and $^{13}$C NMR, thin-layer chromatography (Rf=0,47), and elemental analysis (Anal. Calcd for C$_{15}$H$_{29}$NO$_7$: C, 53.71 ;H, 8.71. Found: C, 53.64; H, 8.86).

The reaction scheme for the synthesis of HECAMEG is summarized below.

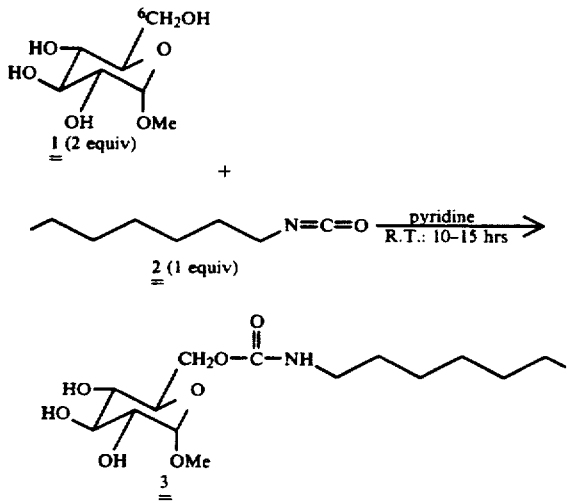

1 (2 equiv) + 2 (1 equiv) → 3

In this procedure, the primary hydroxyl of methyl-α-D-glucoside 1 adds specifically to heptylisocyanate 2 in pyridine, at room temperature for 10 to 15 h; the preliminary protection of the secondary hydroxyl groups is not necessary in the present case. In this reaction, the carbamate 3 is obtained without by-products, except for a small amount of dihepotylurea resulting from partial hydrolysis of the starting isocyanate. 2. Carbamate 3 is very soluble in water and organic solvents such as alcohols, methylene chloride, tetrahydrofuranne, or dimethyl sulfoxide (DMSO). Its structure was deduced from a combination of elemental analysis and spectral data. In the infrared spectrum (hexachlorobutadiene), the carbomoyl group was characterized by a strong absorption band located at ∂, 1685 $cm^{-1}$ and a NH absorption band at 3340 $cm^{-1}$. In the $^1H$ NMR spectrum obtained in deuterated DMSO, the resonance at δ4,55 ppm (J = 3 Hz) represents the anomeric proton of an α-glucoside and the resonance of the primary hydroxyl (at about δ4.70 pmm) did not show up. In the $^{13}C$ NMR spectrum (solvent DMSO-$d_6$) the resonances of the carbohydrate moiety are found downfield of tetramethylsilane at δ99.71 (C1), 73.30, 71.90, 70.46, 69.97 (C2-C5), 63.66 (C6), and 54.39 (OCH$_3$). For the carbamoyl moiety, $^{13}C$ NMR data are δ156.27 (C=O), 40.30, 31.29, 29.48, 28.45, 26.25, 22.08 (CH$_2$), and 13.90 (CH$_3$). The pure compound exhibited a very low absorbance above 250 nm.

EXAMPLE 2

Solubility in water, critical micellar concentration and dializability of HECAMEG HECAMEG proved to be soluble in water and usual buffers (e.g. Tris-Hcl and phosphate buffers) at concentrations up to at least 0,2 M even at 0° C. Furthermore the solutions were stable for several weeks at 4° C.

Determination of CMC

The CMC of HECAMEG was colorimetrically determined with the iodine method of Ross and Olivier and the Coomassie blue G method of Rosenthal and Koussaie and spectrofluorometrically with the technique of Vendittis et al. In the latter case, excitation was performed at 370 nm and emission recorded at 490 nm.

The CMC of the detergent was estimated by three distinct spectrophotometric methods of OG (n-octyla-D glucopyranoside) was used for comparison. The iodine spectrophotometric assay indicated a CMC of 17 mM while values of 14.5 and 15 mM were obtained with Coomassie blue G, and 19.5 mM was obtained by spectrofluorometry at 4° and 20° C. The second method was not reliable with OG, while the two other methods indicated for this surfactant, as expected, a CMC of 25 mM.

Detergent dialysis

Dialysis experiments with HECAMEG were performed with the Lipoprep apparatus using a three-compartment Teflon cell with two cellulose dialysis membranes (molecular mass cutoff 5 kDa). The central compartment was filled with 8 ml of 30 mM HECAMEG in 50 mM Na phosphate buffer, pH 7.4. The same buffer, but without detergent circulated through the two side compartment for 24 h at 25° C. Dialysis speed was estimated by measuring HECAMEG concentration within the central cell.

The dialyzability of HECAMEG was estimated by the use of the Lipoprep dialysis system under conditions corresponding to those used for the preparation of liposomes. Titration of the surfactant in the dialysis cell showed a high dialysis speed. Indeed, the concentration of HECAMEG in the central compartment of the cell dropped by 50% upon 3 h of dialysis and the surfactant was no longer detected after about 18 h.

EXAMPLE 3

Extraction of Bacteria's Membrane Proteins.

Growth and Fractionation of Bacteria

Spiroplasma melliferum B88 was cultivated and membranes were purified as described. The purple membrane of Halobium $R_1$ was purified according to Oesterhelt and Stoeckenius (22). Pasteurella multocida was cultivated in liquid medium containing per liter 20 g of Tryptose (Difco), 1 g of glucose, 5 g of NaCl, and 2,5 g of yeast extract (Difco), pH 7.4. The cells were harvested by centrifugation and disrupted with a French press. Plasma membranes were isolated according the technique of Osborn and Munson.

Membrane Protein Extraction with Detergents

In order to extract membrane proteins, 200 μl of a membrane suspension in 0.1 M Na phosphate buffer (pH 7.4) was mixed with 200 μl of detergent dissolved in water. After 90 min at room temperature, the mixture was centrifuged at 260,000 g for 15 min at 20° C. (Beckman TL-100 ultracentrifuge, TL A 100.1 rotor). The supernatant was recovered for further analysis, while the pellet was dispersed in 400 μl of 2% SDS in 50 mM Tris-HCl buffer (pH 8.0). After 60 min at room temperature, the mixture was centrifuged as above and the supernatant recovered for analysis.

It was possible to extract up to 75% of bacteriorhodopsin from the purple membrane and 40% of protein from the spiroplasmal membrane with 75 mM HECAMEG. This corresponds respectively to ratios of 9 and 26 ug of protein/μmol of detergent. The efficacy of the extraction was not improved by increasing the detergent concentration. It should also be noted that the detergent was inefficient for membrane protein extraction at concentrations below the CMC.

SDS Polyacrylamide Gel Electrophoresis

Since the membrane of melliferum has a complex protein composition, the protein extracted by HECAMEG was analyzed by SDS PAGE. Separation of polypeptides was performed in 100×100×4 mm gels in 40 mM Tris-20 mM Na acetate buffer (pH 7.4) containing 2 mM EDTA and 0.1% SDS. The upper gel contained 4.83% acrylamide and 0.17% bisacrylamide while the lower separating gel contained 7.72% acrylamide and 0.28% bisacrylamide. The samples contained 2% SDS and 0.12 M 2 mercaptoethanol and were heated at 60° C. for 5 min prior to electrophoresis. Bromphenol blue was used as the tracking dye. Protein bands were stained with Coomassie blue R-250 in an acetic acid/methanol/water mixture (1/4/5,v/v). Extraction proved highly selective in favor of spiralin, the main protein of this membrane. Optimal selectivity was obtained with surfactant concentration in the 60 to 65 mM range. Under these conditions, only 12 polypeptides (including spiralin) of 28 detected in the membrane were extracted, most of them with a low efficiency, while spiralin was quantitatively solubilized. It should be noted that higher concentrations of HECAMEG slightly decreased the electrophoretic mobility of spiralin and this surfactant was not able to solubilize the fibril protein.

Crossed Immunoelectrophoresis

Antibodies directed against the S. melliferum membrane were prepared in rabbits as described. The hyperimmune sera were filtered through 0.45-μm-pore membranes and stored at −25° C. Crossed immunoelectrophoresis was performed according to the method of Laurell in 1% agarose gel in veronal buffer, pH 8.6 (I=0.03). After unprecipitaded proteins where eluted and gels were dried, immunoprecipitates were stained with Coomassie blue R-250. Spiralin remained highly antigenic after solubilization with HECAMEG since sharp and heavy immunoprecipitates were obtained in crossed immunoelectrophoresis.

EXAMPLE 4

Effect of HECAMEG on the Absorbance Spectrum of Bacteriorhodopsin

Absorbance of dark-adapted bacteriorhodopsin was recorded between 350 and 700 nm. The untrated (native) purple membrane of H. halobium exhibited an absorption maximum at 558 nm. When the membrane was solubilized with 1% SDS, leading to the extensive denaturation of bacteriorhodopsin, the absorbance at 558 nm was lost to the benefit of a new maximum at 390 nm, corresponding to free retinal dissolved in SDS. These two spectra were thus representative, respectively, of the native and denatured forms of bacteriorhodopsin. Upon extraction with HECAMEG, the absorption spectrum of the protein was similar to that of the native state protein with, however, a slight blue shift in the absorption maximum ($\lambda$max=550 nm). Some absorption was also recorded at 390 nm, but it was much lower than that in SDS, even when HECAMEG was used at concentrations up to 0.1 M. Because of the scatering of light by membrane particles, the 390-nm peak could not be observed in untreated samples.

EXAMPLE 5

Effect of HECAMEG on Enzyme Activities

Enzyme Assays

P. multocida succinate dehydrogenase was assayed as described by Osborn et al in 50 nM Na phosphate buffer (pH 7.4) containing 10 mM KCN, Na succinate (concentration range: 0.25 to 25 mM), 30 ug of thiazolyl blue, and 10 μg of phenazine methosulfate per milliliter. The samples contained 25, 50, or 100 μg of plasma membrane protein per milliliter and the absorbance at 550 nm was recorded for 10 min at 25° C.P. multocida NADH oxidase was assayed in 50 mM Tris-HCl buffer (pH 8.0) containing 0.2 mM dithiothreitol and 0.12 mM NADH. The samples contained 50,75, or 100 μg of plasma membrane protein per milliliter and the absorbance at 340 nm was recorded as above. The activity of the soluble form of Escherichia coli β-lactamase was measured by using Nitrocefin as substrate and by monitoring the rate of increase in the absorbance at 488 nm for 3 min at 25° C. One milliliter of 20 mM Na phosphate buffer (pH 7.4) contained Nitrocefin (concentration range: 5 to 20 uM) and 0.76 ug (i.e., $2\times10^{-3}$ units) of β-lactamase.

Bovine milk lactoperoxidase was assayed according to George except that o-dianisidine was used as the substrate instead of gaiacol. One milliliter of 20 mM Na phosphate buffer (pH 7.4) contained $H_2O$ (concentration range: 0.06 to 0.9 mM) 1 mM o-dianisidine, and $25\times10^{-3}$ μg (i.e., $1.15\times10^{-3}$ units) of lactoper oxidase. The absorbance at 435 nm was recorded as for β-lactamase.

The four enzyme activities were measured in the absence of surfactants and in the presence of 3 or 30 mM HECAMEG. Controls were also performed with 35 mM SDS. Km and V max were determined from Lineweaver-Burk plots, each point being the average of three estimations.

In order to assess the effect of HECAMEG on enzymatic activities, two soluble enzymes (β-lactamase and lactoperoxidase) and two membrane enzymes (NADH oxidase and succinate dehydrogenase) were used. The results are summarized in Table 1.

TABLE 1

| | EFFECT OF HECAMEG ON THE $K_m$ AND $V_{max}$ OF ENZYMES | | | |
|---|---|---|---|---|
| | HECAMEG | | $K_m \pm$ SD | $V_{max} \pm$ SD |
| ENZYME | % | mM | (μM) | (μmol/min) |
| Succinate dehydrogenase | 0 | 0 | 982 ± 44 | 161 ± 32 |
| | 0.1 | 3 | 947 ± 52 | 163 ± 41 |
| | 1 | 30 | 901 ± 65 | 357 ± 50 |
| NADH oxidase | 0 | 0 | 12.5 ± 0.9 | 4.0 ± 0.3 |
| | 0.1 | 3 | 12.5 ± 1.2 | 4.0 ± 0.5 |
| | 1 | 30 | 3.3 ± 0.6 | 10.3 ± 1.2 |
| β-Lactamase | 0 | 0 | 35.5 ± 2.4 | 88.9 ± 1.9 |
| | 0.1 | 3 | 62.0 ± 10 | 143 ± 16.5 |
| | 1 | 30 | 18.1 ± 0.6 | 30.5 ± 0.4 |
| Lactoperoxidase | 0 | 0 | 197 ± 8 | $(356 \pm 0.5) \times 10^{-3}$ |
| | 0.1 | 3 | 182 ± 8 | $(609 \pm 30) \times 10^{-3}$ |
| | 1 | 30 | 425 ± 25 | $(1238 \pm 4) \times 10^{-3}$ |

In the case of the two membrane-associated enzymes, neither Km nor Vmax was significantly modified by the detergent below the CMC. However, when HECAMEG was used above the CMC, the Vmax increased for each enzyme since it was shifted from 161 to 357 μmol/min and from 4 to 10.3 μmol/min for succinate dehydrogenase and NADH oxidase, respectively. Furthermore, the affinity of the latter enzyme for its substrate was increased fourfold since the Km was shifted from 12.5 to 3.3 μM. When membrane samples were treated with 30 mM HECAMEG and then ultracentrifuged, the activities of NADH oxidase and succinate dehydrogenase were detected exclusively in the soluble fractions. Upon treatment with SDS, both enzymes were completely inhibited, which was expected because of the denaturing properties of this surfactant.

In case of the two soluble enzymes, apparent activation occurred with HECAMEG below the CMC while opposite effects were observed above the CMC. Indeed, with 30 mM surfactant, the Vmax was decreased threefold for β-lactamase and increased about threefold for lactoperoxidase. It was observed that the spectral properties of Nitrocefin and the product of the reaction were modified by HECAMEG since absorption maxima were, respectively, shifted up from 393 to 400 nm and from 448 to 513 nm. In the case of lactoperoxidase, although the spectral properties of o-dianisidine were not modified by HECAMEG, even above the CMC, the maximum of absorption of the product was shifted from 520 down to 440 nm. In comparison, both enzymes were fully inhibited by SDS.

EXAMPLE 6

Titration of HECAMEG by Anthrone Method

HECAMEG was titrated with the anthrone method according to Germyn.

Since the hydrophilic part of HECAMEG is a glucoside, we have assessed the possibility of using the anthrone method for the titration of this surfactant. As with glucose and saccharose, a good linearity was accorded up to 0.5 mM detergent when concentration was plotted vws absorbance. Therefore, this method may confidently used for the titration of HECAMEG with glucose as standard.

What is claimed is:

1. A process for extracting surface membrane proteins without denaturating said proteins from bacterial microorganisms present in an aqueous membrane suspension, comprising contacting said membrane suspension with an extraction-effective amount about the CMC of at least one surfactant for a sufficient period of time to extract said surface membrane proteins, said surfactant being a non ionic surfactant having the formula (1):

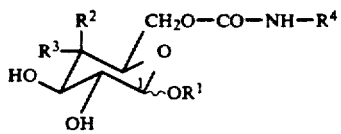

wherein
$R^1$ is H or $CH_3$;
$R^2$ is H or OH;
$R^3$ is H or OH;
$R^4$ is an alkyl radical of formula $(CH_2)_n-CH_3$, wherein n is an integer between 6 and 20 and recovering said proteins therefrom.

2. Process as claimed in claim 1, wherein surfactant is 6-0-(N-Heptylcarbamoyl) methyl-α-D glucopyranoside.

3. Process as claimed in claim 1, wherein microorganisms are selected from the group consisting of *Halobacterium halobium*, *Spiroplasma melliferum* and *Pasteurella multocida*.

* * * * *